(12) United States Patent
Migliaccio et al.

(10) Patent No.: US 10,136,810 B2
(45) Date of Patent: Nov. 27, 2018

(54) SYSTEMS AND METHODS FOR DIAGNOSIS AND THERAPY OF VISION STABILITY DYSFUNCTION

(71) Applicants: Neuroscience Research Australia (NeuRA), Randwick (AU); The Johns Hopkins University, Baltimore, MD (US)

(72) Inventors: Americo A. Migliaccio, Kingsford (AU); Michael C. Schubert, Parkton, MD (US)

(73) Assignees: NEUROSCIENCE RESEARCH AUSTRALIA (NEURA), Randwick, New South Wales (AU); THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/026,900

(22) PCT Filed: Aug. 26, 2014

(86) PCT No.: PCT/AU2014/000843
§ 371 (c)(1),
(2) Date: Apr. 1, 2016

(87) PCT Pub. No.: WO2015/048839
PCT Pub. Date: Apr. 9, 2015

(65) Prior Publication Data
US 2016/0242642 A1    Aug. 25, 2016

(30) Foreign Application Priority Data

Oct. 3, 2013   (AU) ................................ 2013903822

(51) Int. Cl.
*A61B 3/14*      (2006.01)
*A61B 3/10*      (2006.01)
(Continued)

(52) U.S. Cl.
CPC ............ *A61B 3/113* (2013.01); *A61B 3/0025* (2013.01); *A61B 3/0091* (2013.01); *A61B 3/145* (2013.01);
(Continued)

(58) Field of Classification Search
CPC .. A61B 3/156; A61B 3/14; A61B 3/12; A61B 3/158; A61B 3/152
(Continued)

(56) References Cited

U.S. PATENT DOCUMENTS 9,072,481 B2    7/2015  Shelhamer
2002/0105482 A1  8/2002  Lemelson et al.
(Continued)

FOREIGN PATENT DOCUMENTS

WO    WO-2013/117727 A1    8/2013

OTHER PUBLICATIONS

International Preliminary Report on Patentability in PCT International Application No. PCT/AU2014/000843, dated Feb. 3, 2016.
(Continued)

*Primary Examiner* — Mohammed Hasan
(74) *Attorney, Agent, or Firm* — Henry J. Daley; Venable LLP

(57) ABSTRACT

Described herein are improved systems and methods for diagnosis and therapy of vision stability dysfunctions in a patient. One embodiment provides a device (1) for obtaining data from a patient (3). Device (1) includes a frame (5) configured for mounting to the patient (3), a target module (8) for providing a drive signal to define a selectively movable target object, an eye tracking module (12) mounted to the frame (5), the module (12) being responsive to the drive signal for obtaining first data indicative of one or more characteristics of the patient's eyes; and a head tracking module (16) mounted to the frame (5), the head tracking
(Continued)

module (16) being responsive to the drive signal for obtaining second data indicative of one or more characteristics of the motion of the patient's head.

24 Claims, 11 Drawing Sheets

(51) Int. Cl.
```
A61B 3/113    (2006.01)
A61B 5/00     (2006.01)
A61B 5/11     (2006.01)
G06F 3/01     (2006.01)
A61B 3/00     (2006.01)
A61H 5/00     (2006.01)
G02B 5/28     (2006.01)
G06F 19/00    (2018.01)
G16H 40/67    (2018.01)
```
(52) U.S. Cl.
CPC .......... *A61B 5/0022* (2013.01); *A61B 5/1114* (2013.01); *A61B 5/6803* (2013.01); *A61B 5/742* (2013.01); *A61H 5/00* (2013.01); *G02B 5/282* (2013.01); *G06F 3/012* (2013.01); *G06F 3/013* (2013.01); *G06F 19/00* (2013.01); *G16H 40/67* (2018.01); *A61B 2505/09* (2013.01); *A61B 2562/0219* (2013.01); *A61B 2562/0223* (2013.01); *G06F 2203/011* (2013.01); *G09G 2380/08* (2013.01)

(58) Field of Classification Search
USPC .................................................. 351/200–246
See application file for complete search history.

(56) References Cited

U.S. PATENT DOCUMENTS

| | | | |
|---|---|---|---|
| 2004/0156554 A1* | 8/2004 | McIntyre | G06T 5/00 382/254 |
| 2009/0240172 A1* | 9/2009 | Fernandez Tournier | G09B 7/04 600/595 |
| 2010/0198104 A1 | 8/2010 | Schubert et al. | |
| 2012/0293773 A1* | 11/2012 | Publicover | A61B 3/113 351/210 |
| 2016/0007849 A1* | 1/2016 | Krueger | A61B 3/113 600/301 |
| 2016/0262608 A1* | 9/2016 | Krueger | A61B 3/0041 |

OTHER PUBLICATIONS

International Search Report in PCT International Application No. PCT/AU2014/000843, dated Nov. 19, 2014.

Schubert et al., "Mechanism of Dynamic Visual Acuity Recovery with Vestibular Rehabilitation," Arch Phys Med Rehibil, 89(3), pp. 500-507, Mar. 2008.

\* cited by examiner

SYSTEMS AND METHODS FOR DIAGNOSIS AND THERAPY OF VISION STABILITY DYSFUNCTION

FIELD OF THE INVENTION

The present invention relates to improved methods and systems for the diagnosis and therapy of vision stability dysfunction. While the systems have been developed primarily for use in vestibular-visual programs, various aspects of the invention also extend to other applications including the use of visual only programs.

This application is a U.S. National Stage Application under 35 U.S.C. § 371 of PCT/AU2014/000843, filed on Aug. 26, 2014, and claims the benefit of Australian Patent Application No. 2013903822, filed Oct. 3, 2013.

BACKGROUND OF THE INVENTION

Loss of balance in humans is known to often result from dysfunction associated with the peripheral vestibular organs of the inner ear. Issues relating to loss of balance can lead to injuries, permanent debilitation and even death.

The vestibular organs define a vestibular system which is central to balance control in humans. The paired vestibular systems or organs are housed within the temporal bone on either side of the head. Each vestibular system includes three orthogonal semicircular canals and two otolith organs known as the utricle and the saccule. Together these elements provide continuous input to the brain about rotational and translational head movement, as well as the detection of gravity. The information allows for the maintenance of retinal image stability and gaze stability via the reflexive eye movement known as the vestibulo-ocular reflex (VOR). The VOR generates compensatory eye movements during sudden head movements to maintain visual stability. For example, if the head pitches nose-down at a velocity of 100° per second, as occurs during running, then during typical viewing (i.e., optical infinity) the eyes are rotated up at the same velocity. The end result is that the angular position of the eyes in space (gaze) remains fixed (i.e., zero gaze velocity), as does the visual image on the retina. Without this reflex eye movement, stable vision becomes difficult or impossible during head movement.

Vestibular dysfunction on one or both sides (unilateral or bilateral) due to age or injury is very common. This dysfunction often results in dizziness, vertigo and imbalance due to disturbances in gaze and postural stability, which can result in reduced mobility and even serious injury due to falls.

Until recently, all systems, programs and devices for vestibular rehabilitation, such as that proposed by Herdman S J, Schubert M C, Das V E, Tusa R J. (2003) ("Recovery of dynamic visual acuity in unilateral vestibular hypofunction" *Arch Otolaryngol Head Neck Surg.* 129:819-824) can require repetitive lengthy exercises of 40 to 50 minutes per session 4 to 5 times a day to achieve fairly modest functional VOR improvements of on average 5% after 6 to 8 weeks.

Significant improvements in these results have been achieved with the methods and systems proposed in US Patent Application Publication US 2010/0198104 to Schubert et al. and entitled "System for Diagnosis and therapy of gaze stability". However, the system hardware described in Schubert et al. has limitations in terms of monitoring a patient's actual eye movement during assessment and rehabilitation, measuring and monitoring responses during head movement in planes other than the horizontal plane, and facilitating remote intervention, assessment and program planning by a clinician situated at a location geographically removed from that of the patient.

Similarly, while the described rehabilitation methods appeared to work well for treatment of the damaged side undergoing adaptation, the process appeared to also affect the undamaged untreated side, thereby reducing the overall effectiveness of the treatment in terms of achieving a balanced normal response from both sides.

Further, there is currently no known manner to assess the effectiveness or appropriateness of settings during the exercises.

It is an object of the present invention to provide one or more methods or systems which overcome or ameliorate the deficiencies of the prior art, or which at least offer a useful alternative.

SUMMARY OF THE INVENTION

According to a first aspect of the invention, there is provided a device for obtaining data from a patient having a head and at least one eye, the device including:
 a frame configured for mounting to the patient;
 a target module responsive to a drive signal to define a selectively movable target object;
 an eye tracking module mounted to the frame, the module being adapted for obtaining first data indicative of one or more characteristics of the at least one eye; and
 a head tracking module mounted to the frame, the head tracking module being adapted for obtaining second data indicative of one or more characteristics of the motion of the head.

The device preferably includes an analysis module that is responsive to the drive signal and at least a subset of both the first data and the second data for providing an indication of retinal image stability for the patient. The indication of retinal image stability preferably includes one or more of the visual, non-visual, sinusoidal or impulse vestibulo-ocular reflex gain, nystagmus, phase and latency, compensatory saccade amplitude, compensatory saccade latency, smooth pursuit gain, latency and phase.

The analysis module is preferably remote from the frame. The device preferably includes a communications module for communicating at least the subset of both the first and second data to the analysis module. The communications module is preferably mounted to the frame.

The analysis module preferably includes an external processor and the communications module is preferably configured for transferring the first data and the second data from the device to the external processor, the external processor being configured for processing the first data and the second data to generate an indication of retinal image stability for the patient.

The communications module preferably communicates wirelessly with the external processor. The external processor preferably includes one or more of a computer, tablet, PDA or Smartphone having software configured to process the first and second data to generate an indication of retinal image stability for the patient.

The target module preferably includes a laser configured to project at least one laser beam onto a surface in front of the patient to define the target object. The direction of the at least one laser beam is preferably electrically controllable by the drive signal. The drive signal is preferably generated in response to the motion of the head detected by the head tracking module.

The target module preferably includes a mirror located in the path of the at least one laser beam, the mirror being responsive to the drive signal to selectively electrically tilt in at least a first dimension and thereby move the target object in that first dimension. The mirror is preferably responsive to the drive signal to selectively electrically tilt in two dimensions and thereby move the target object in two dimensions.

The laser preferably projects the beam along an axis that is substantially parallel to a first dimension of the surface and the mirror is oriented at an angle of substantially 45 degrees to the first dimension of the surface to thereby project the at least one laser beam substantially perpendicularly onto the surface.

The eye tracking module preferably includes one or more cameras positioned to capture video images of the at least one eye. The one or more characteristics of the at least one eye preferably include the eye gaze direction. The eye tracking module preferably includes one or more hot mirrors that transmit visible radiation and reflect infra-red radiation.

The one or more cameras are preferably configured to detect infra-red images of the at least one eye reflected off the one or more hot mirrors. The one or more hot mirrors are preferably positioned in the line of sight between the at least one eye and the target object, and the one or more cameras are positioned out of the line of sight between the at least one eye and the target object.

The eye tracking module preferably includes a pair of hot mirrors and a pair of cameras oppositely disposed on the frame for simultaneously measuring first data for both a left and right eye of the patient.

The frame preferably includes a mount for maintaining one of the hot mirrors in the line of sight of a respective one of the left and right eyes, the mount further maintaining the cameras at peripheral positions outside the lines of sight of the left and right eyes.

The device preferably includes a housing attached to the mount for containing one or both of the target module and the head tracking module.

The head tracking module preferably includes one or more gyroscopes. Preferably a gyroscope is configured to measure the one or more characteristics of the motion of the head in three dimensions. The one or more characteristics of the motion of the head preferably includes the angular velocity of the head. The one or more characteristics of the motion of the head preferably includes the angular acceleration of the head.

The head tracking module preferably includes a magnetometer. The one or more characteristics of the motion of the head preferably includes the static direction/orientation of the head. The magnetometer is preferably configured to measure the one or more characteristics of the motion of the head in three dimensions.

The head tracking module preferably includes an accelerometer. The accelerometer is preferably configured to measure the orientation of the head with respect to gravity and/or the translational acceleration of the head.

The frame preferably includes an adjustable support strap projecting from the frame and being adapted to extend peripherally around the patient's head in use for supportively securing the device to the patient.

The device preferably includes a speaker for providing audible instructions to the patient for performing an action.

In one embodiment, the drive signal is derived from motion of the head detected by the head tracking module.

In one embodiment, the target module includes a display for displaying a virtual reality scene about the user and the target object is a virtual target within that scene.

According to a second aspect of the invention, there is provided a system for measuring a retinal image stability of a patient, the system including:

a measurement device adapted to be worn by the patient, the measurement device including a sensor module for obtaining data indicative of one or more characteristics of at least one eye of the patient and the head of the patient during a physical action by the patient in response to a stimulus from a target object; and a control module in communication with the measurement device for processing data indicative of the one or more characteristics during the physical action to provide an indication of the retinal image stability for the patient.

The system preferably includes a target module responsive to a drive signal to define the target object, which is selectively movable to be tracked by the patient's eyes.

The sensor module preferably includes a head motion sensor for measuring head motion characteristics and providing the drive signal. The one or more characteristics preferably includes the gaze direction of the at least one eye during the physical action. More preferably, the one or more characteristics includes the position of the head during the physical action. The indication of retinal image stability preferably includes one or more of the visual, non-visual sinusoidal or impulse vestibulo-ocular reflex gain, nystagmus, phase and latency, compensatory saccade amplitude, compensatory saccade latency, smooth pursuit gain, latency and phase.

The control module is preferably adapted to communicate with an interface for prompting the patient to perform a specific physical action from a number of predefined physical actions. The control module preferably includes an interface for prompting the patient to perform a specific physical action from a number of predefined physical actions.

Preferably, the interface visually prompts the patient to perform the physical action. Preferably, the interface also audibly prompts the patient to perform the physical action. In some embodiments, the physical action preferably includes a substantially horizontal rotation of the head in a predefined direction. In other embodiments, the physical action preferably includes a substantially vertical rotation of the head in a predefined direction. In some embodiments, the physical action preferably includes a substantially horizontal rotation of the at least one eye in a predefined direction. In other embodiments, the physical action preferably includes a substantially vertical rotation of the at least one eye in a predefined direction.

The control module preferably includes one or more of a computer, tablet or Smartphone having a visual display and data input control. The control module preferably includes software configured to remotely control the target module. The target module preferably includes a laser configured to project at least one laser beam onto a surface in front of the patient to define the target object. The software preferably remotely controls the at least one laser beam direction to selectively move the position of the projected at least one laser beam along a predetermined trajectory.

The control module preferably communicates over a network or the Internet to transmit data obtained from the measurement device to a third party device.

According to a third aspect of the invention, there is provided a method of improving the vestibulo-ocular response for patients with unilateral hypofunction in a first side, the method including the steps of:

a) inducing a patient head to move in a first direction corresponding to the first side requiring adaptation;

b) configuring one or more sensors to measure the patient's head motion velocity in that first direction and generating a first signal indicative of the patient's head motion velocity in that first direction;

c) in response to the first signal, electronically moving a visual target, with respect to the patient's head, in a direction opposite to the first direction at a first velocity that is a function of the patient's head motion velocity in the first direction and having the patient visually fixate on the moving visual target;

d) inducing the patient's head to move in a second direction corresponding to the second non-adapting side;

e) configuring the one or more sensors to measure the patient's head motion velocity in that second direction and generating a second signal indicative of the patient's head motion velocity in that second direction; and f) in response to the second signal, deactivating the visual target or electronically moving a visual target, with respect to the patient's head, in a direction opposite to the second direction at a second velocity that is substantially the same as the patient's head motion velocity in the second direction and having the patient visually fixate on the moving visual target.

The method preferably also includes the step of:

g) iteratively repeating steps a) to f) and incrementally increasing or decreasing the first velocity at each iteration.

According to a fourth aspect of the invention, there is provided a device for obtaining data from a patient having a head and at least one eye, the device including:

a target module responsive to a drive signal to define a selectively movable target object;

an eye tracking module, the module being adapted for obtaining first data indicative of one or more characteristics of the at least one eye; and a head tracking module, the head tracking module being adapted for obtaining second data indicative of one or more characteristics of the motion of the head.

BRIEF DESCRIPTION OF THE DRAWINGS

Embodiments of the invention will now be described, by way of example only, with reference to the accompanying drawings in which.

DETAILED DESCRIPTION

Overview of Headwear Device

Figure 1:
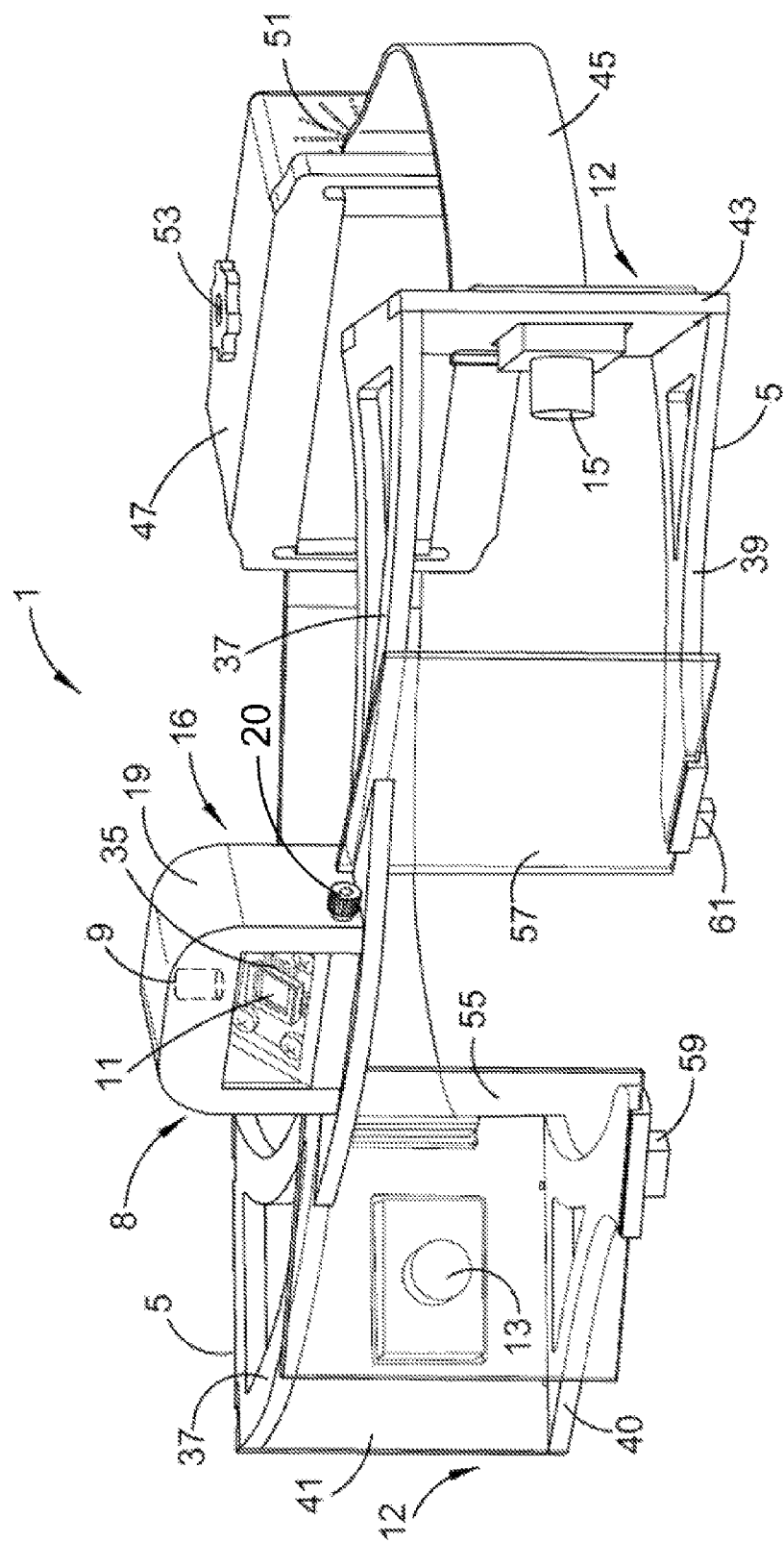
FIG. 1 illustrates a front elevated perspective view of a device for obtaining eye motion and head motion data from a patient.

Referring to FIGS. 1 to 5, there is illustrated a device 1 for obtaining data from a patient 3. The device is particularly adapted for diagnosis and rehabilitation in relation to the retinal image stability and vestibulo-ocular reflex (VOR) of the patient. As such, device 1 will be described herein with reference to this application. However, it will be appreciated that device 1 is also compatible with other applications.

Device 1 includes a frame 5 configured for mounting to patient 3, about the patient's head 7. An internal target module 8, including a laser 9 and electro-mechanically tiltable mirror 11, is responsive to a drive signal to define a selectively movable target object. An eye tracking module 12, in the form of a pair of eye-monitoring cameras 13 and 15, is mounted to the frame, and is adapted for obtaining first data indicative of one or more motion characteristics of the patient's two eyes (hereinafter referred to as eye motion data) when tracking the target object. A head tracking module 16, in the form of one or more motion sensors (not shown), is also mounted to the frame. The head tracking module is adapted for obtaining second data indicative of one or more characteristics of the motion of the patient's head (hereinafter referred to as head motion data). Target module 8 is responsive to the patient's head motion as measured by head tracking module 16. That is, upon detection of the movement of the patient's head by module 16, target module 8 is actuated to move the target object. In other embodiments, target module 8 is initiated by other stimuli.

Figure 5:
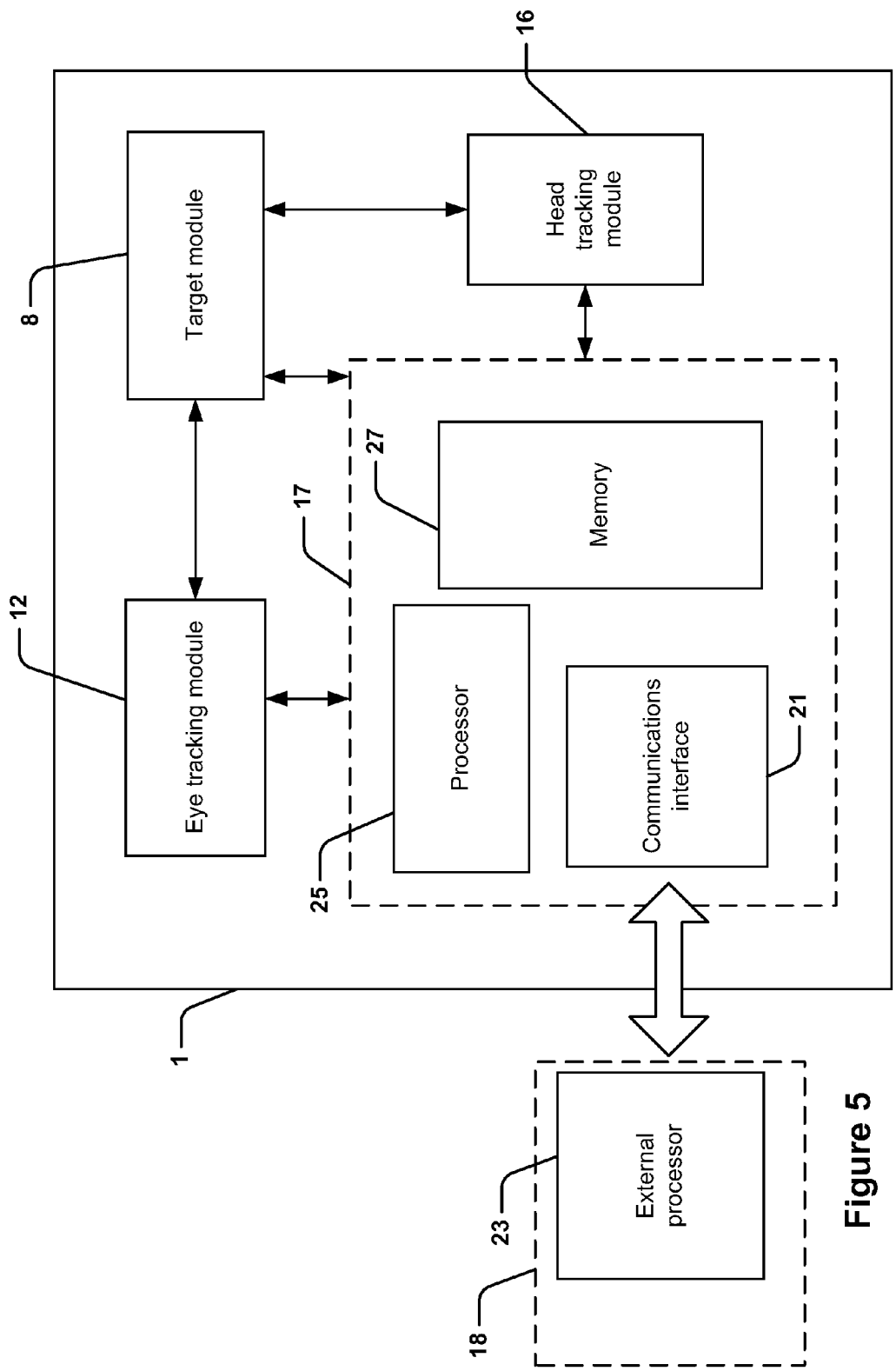
FIG. 5 illustrates a schematic block diagram of the device of FIG. 1.

As shown in FIG. 5, device 1 includes an external analysis module 18 that is responsive to at least the position of the target object and a subset of one or both of the eye motion data and the head motion data for providing an indication of retinal image stability for the patient. Retinal image stability is a measure of the stability of images as seen by a person's retina. A subset measure of retinal image stability is the well-known measure of gaze stability. Indications of retinal image stability and gaze stability measured with the analysis module of device 1 include one or more of the visual/non-visual (i.e., VOR measured in light or dark) sinusoidal/impulse (i.e., VOR measured during bi- or uni-directional head movements) VOR gain, VOR nystagmus, VOR phase and VOR latency, compensatory saccade amplitude, compensatory saccade latency, smooth pursuit gain, smooth pursuit latency and smooth pursuit phase.

VOR gain is a measure of the ratio of eye velocity magnitude to head velocity magnitude (eye velocity/head velocity) in response to a head velocity stimulus. The typical gain of a normal human (without dysfunction) during typical viewing is unity. Nystagmus is the combined VOR eye movement (known as the slow-phase) and resetting eye movement (that brings the eye back to the centre of its oculomotor range, known as the quick-phase), which typically occurs during sustained head motion. The presence of nystagmus can be used to diagnose vestibular disorders, for example, nystagmus that occurs after repeated left-right-left head shaking, known as head shaking nystagmus, indicates asymmetric function between the two vestibular organs. Latency is the time required for the eyes to respond to a motion of the head so as to maintain retinal image stability during the head motion. Compensatory saccades are fast corrective eye movements that are performed during a head movement to stabilise a patient's vision. The patient's compensatory saccade reacquires the visual target that the patient has lost during a rapid head movement as a result of their poorly functioning VOR. Both the amplitude and latency of a patient's compensatory saccades are an indication of the patient's retinal image stability.

Figure 2:
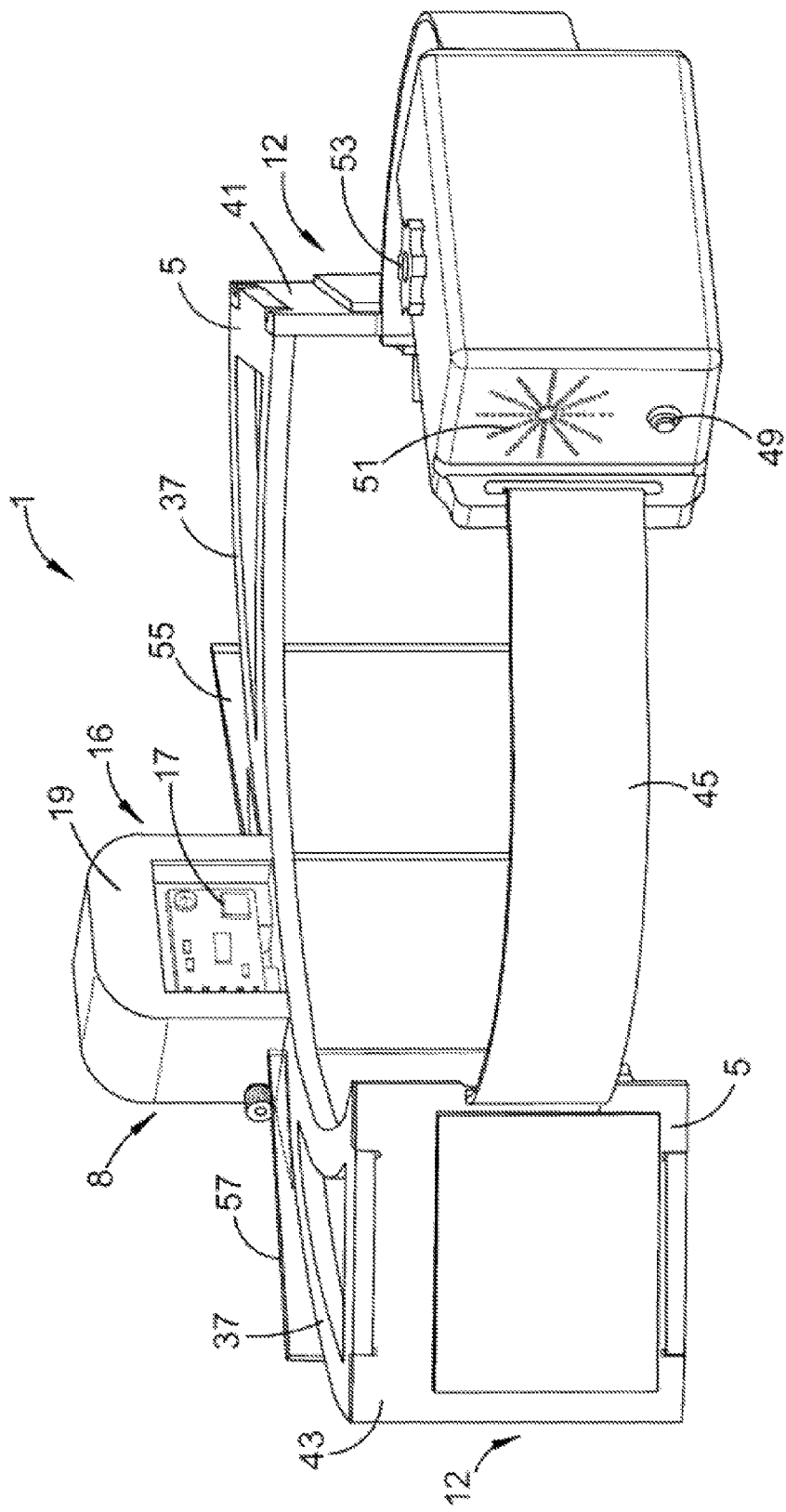
FIG. 2 illustrates a rear perspective view of the device of FIG. 1.

Device 1 includes an integrated circuit (IC) 17, as shown in FIG. 2, which includes a number of elements configured to perform different functions, including head tracking module 16. IC 17 is located within a tiltable housing 19 that is mounted to an upper region of frame 5 and held firm with an adjustable thumbscrew 20. Housing 19 is selectively manually tiltable with respect to frame 5 so as to adjust the direction of laser 9 when the laser is in its neutral position. As shown in FIG. 5, IC 17 includes a communications module in the form of a communications interface 21 for communicating at least the subset of both the eye motion data and head motion data to external analysis module 18. Communications interface 21 includes communication components such as an Internet connection, modem, Ethernet port, serial port, wireless device, Bluetooth device or the like. The external analysis module includes an external processor 23 and communications interface 21 is configured for transferring the eye motion data and the head motion data from device 1 to external processor 23. External processor 23 is configured for processing the target, eye and head motion data to generate the indication of retinal image stability for the patient. IC 17 also includes an internal processor 25 and a memory module 27 for performing pre-processing and temporary storage/buffering of obtained data respectively.

Communications interface 21 is configured to communicate wirelessly with external processor 23 through one or more known wireless communication techniques. However, in other embodiments, communications interface 21 is able to be connected by electrical cable to external processor 23 through respective electrical ports (not shown). In various embodiments, external processor 23 is able to be utilised on one or more of a personal computer (PC), tablet, PDA or Smartphone. The appropriate computer device has software installed that is configured to process the head motion data, eye motion data and the target object position data to generate an indication of retinal image stability for the patient. In some embodiments, external processor 23 communicates with communication interface 21 to provide the target drive signal to device 1.

In a further embodiment (not shown), analysis module 18 is integrated onto frame 5 of device 1 and is configured for performing the local processing of at least a subset of the target object position, and one or both of the eye and head motion data for providing an indication of retinal image stability for the patient. The indication generated by the local analysis module is able to be saved on a local database integrated with frame 5 and/or communicated to an external database.

It will be appreciated that, in some embodiments, processing can be shared between processor 25 and external processor 23. Similarly, data storage can be shared between memory 27 and one or more external databases.

In addition to processing the data obtained by device 1, external analysis module 18 also functions as a control module for prompting the patient to perform a predefined action. Further details regarding this functionality and the system associated with device 1 are set out below. In some embodiments, external analysis module 18 also provides a drive signal to device 1.

Target module 8 includes laser 9 configured to project a laser beam 29 onto a surface such as a wall 31 in front of the patient. The adjustability of housing 19 allows the laser beam 29 to be directed substantially perpendicularly (when the laser mirror is in its neutral position) onto wall 31 despite imperfect positioning of frame 5 about the patient's head 7. The resulting projected laser spot 33 defines, at least in part, the target object. In some embodiments, the target object is also defined by one or more other objects or images. In one embodiment, target module 8 projects multiple laser beams and the target object represents multiple spots on wall 31. The multiple beams may move together or independently. In further embodiments, target module 8 includes an image projector for projecting a target object in the form of a video image or scene onto wall 31. In another embodiment, the target module includes a display for displaying a virtual reality type scene about the user and the target object is a virtual target within that scene. As such, the target may be real or virtual.

In typical operation, the patient is positioned such that wall 31 is preferably located at a distance of about 1 m from the patient's eyes and preferably extends substantially vertically and perpendicularly to the patient's substantially horizontal gaze direction. At wall 31, the projected laser spot has a diameter of about 2 mm and represents at least part of the target object to be tracked by the patient. In some embodiments, one or more spatial filters are placed on the laser to project other images onto the surface such as characters or other indicia including full field visual images.

Figure 3:
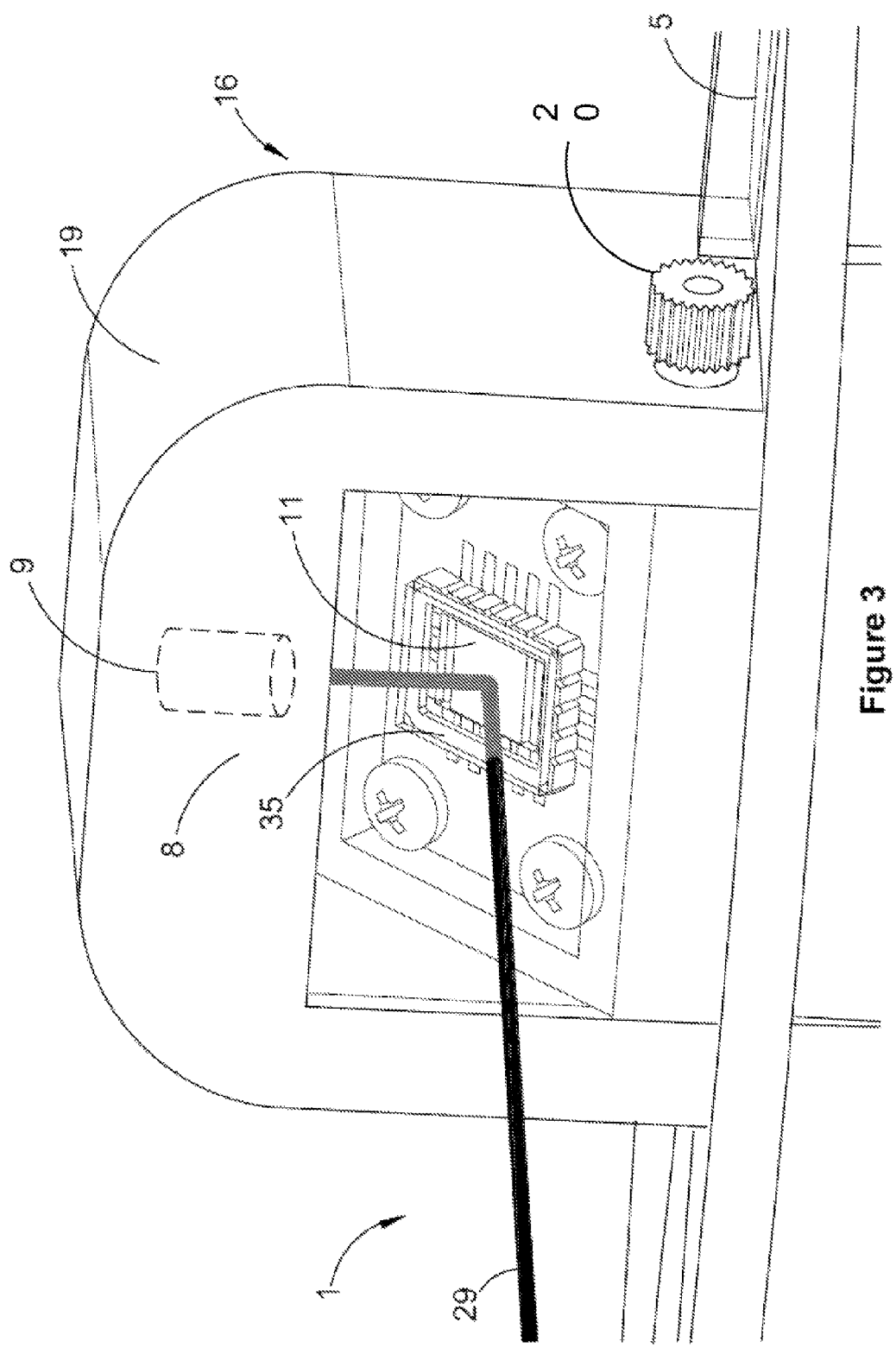
FIG. 3 illustrates a front perspective view of a housing included on the device of FIG. 1, the housing adapted for containing a head tracking module and a target module.

As shown best in FIGS. 1 and 3, laser 9 is situated within housing 19 and is disposed substantially vertically downward when device 1 is worn correctly by patient 3. Beam 29 emerging from laser 9 is incident onto mirror 11 that is located in the path of beam 29 and angled at an angle of about 45 degrees to the horizontal, when device 1 is worn. After reflection off mirror 11, beam 29 propagates substantially horizontally to project laser spot 33 substantially perpendicularly onto the vertically extending wall 31. Here, substantially horizontally means primarily horizontal excluding vertical deviations from the patient's head motion and predetermined vertical beam displacement for the purposes of tracking the patient's eye and head motion in that dimension. Mirror 11 is disposed on a mount 35 that is electrically tiltable to tilt mirror 11 in two dimensions. Mount 35 is responsive to the drive signal provided by the external processor to selectively electromechanically tilt mirror 11 in two dimensions to thereby move laser spot 33 vertically and horizontally across wall 31.

Frame 5 includes upper curved portion 37 and lower curved portions 39 and 40 that extend circumferentially about a front region of the patient's head 7, as best shown in FIG. 1. Upper portion 37 and lower portions 39 and 40 are connected together by respective vertically extending support formations 41 and 43.

An adjustable and flexible support strap 45 extends between support formations 41 and 43 and is adapted to extend peripherally around the patient's head 7 when in use for supportively securing device 1 to patient 3. Strap 45 is connected about a battery module 47 which houses one or more rechargeable batteries (not shown) and provides electrical power to target module 8 and head tracking module 16. Battery module 47 includes a DC power socket 49 for receiving an electrical signal to charge the batteries. The rechargeable batteries housed within module 47 are preferably only rechargeable when device 1 is not in use.

As best shown in FIG. 2, battery module 47 also includes a speaker 51 for receiving a signal from the external processor, through communications interface 21, to provide an audible prompt to patient 3. As will be described below, such audible prompts may be provided to instruct patient 3 to perform a predefined action during which the head motion and eye motion are tracked. The action performed by the patient may be self-induced by following an instruction or prompt (active movement) or may be externally-induced, say by an assistant (passive movement).

Battery module 47 further includes a twist-cap 53 for selectively controlling the tightness of strap 45 around the patient's head 7. The tightness of device 1 on the patient's head 7 is important to minimise the relative slip between device 1 and head 7 during head motion so as to minimise measurement errors.

Cameras 13 and 15 are mounted to respective support formations 41 and 43 and are oriented to capture video images of the right and left eyes respectively. Specifically, the images captured by cameras 13 and 15 are processed to measure the eye gaze direction by tracking the position of the pupil or other eye features over time. Camera 13 is configured to capture images of the patient's right eye and camera 15 is configured to capture images of the patient's left eye. The image processing and pupil tracking algorithms are performed by analysis module 18. However, in other embodiments, these functions are performed at least in part by communications interface 21.

In one exemplary process, cameras 13 and 15, together with analysis module 18, are configured to measure eye rotations about the line of sight. This allows, for example, tracking of iral striations or other ocular landmarks in addition to the pupil tracking.

To avoid visual interference with the patient's tracking of the laser spot, cameras 13 and 15 are positioned at peripheral positions out of the line of sight between the eyes and laser spot 33. A pair of dichroic or 'hot mirrors' 55 and 57 are supported between the upper portion 37 and lower portions 39 and 40 of frame and positioned in the line of sight between the eyes and laser spot 33. Mirror 55 is situated in the line of sight of the patient's right eye and mirror 57 is situated in the line of sight of the patient's left eye. Mirrors 55 and 57 are configured to transmit visible radiation reflected from the laser spot while reflecting infra-red radiation reflected from the eyes. In another embodiment, cameras 13 and 15 are mounted above the patient's eyes and are angled downward to receive infra-red light reflected from mirrors 55 and 57, which are angled upwardly at a predefined angle.

Figure 4:
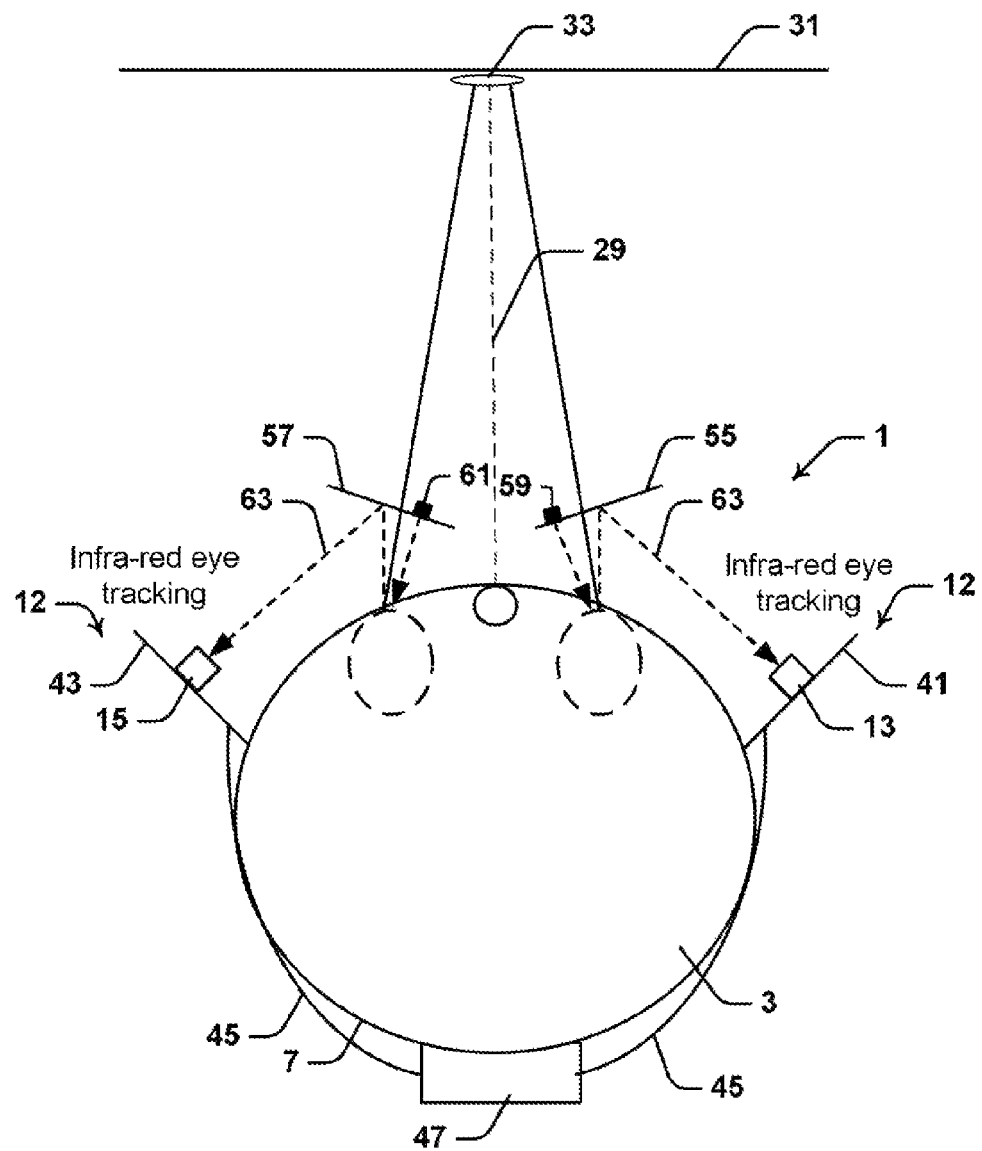
FIG. 4 illustrates a schematic plan view of the device of FIG. 1 in use worn by a patient and projecting a laser beam onto a nearby wall.

As shown in FIGS. 1 and 4, LEDs 59 and 61 are mounted to respective lower portions 39 and 40 below mirrors 55 and 57. LEDs 59 and 61 are configured to emit infra-red radiation 63 onto the respective eyes. As shown in FIG. 4, the infra-red radiation is reflected from each eye onto the respective mirror and then onto the respective camera 13 and 15. This infra-red eye tracking allows measurements using device 1 to be performed in darkness.

Head tracking module 16, which is also disposed within housing 19, includes capability to measure angular head motion with three degrees of freedom, that is, head yaw, pitch and roll, as well as translational head motion in the three Cartesian dimensions. In one embodiment, head tracking module 16 is able to measure angular velocity at a sample rate of 200 Hz.

Module 16 includes a gyroscope configured to measure the angular velocity and the angular acceleration of the patient's head 7 in three dimensions. Head tracking module 16 further includes a magnetometer configured to measure the absolute (Earth coordinates with respect to magnetic north) direction/orientation of the patient's head 7 in three dimensions. Head tracking module 16 also includes an accelerometer configured to measure the patient's head static angular orientation (with respect to gravity) and translational acceleration in three dimensions. In some embodiments, head tracking module 16 is capable of measuring the absolute or relative translational head position and velocity in three dimensions.

Although not illustrated, it will be appreciated that in other embodiments device 1 is not head-mounted to a patient but is separate to the patient. By way of example, an earth-fixed camera system monitors the patient's eyes and head motion, and a laser projection system provides the target laser spot.

Exemplary System Implementations

Device 1 described above is capable of being used in a system, as described below, to perform diagnostic assessment and rehabilitation of the retinal image stability and VOR in a patient.

Figure 6:
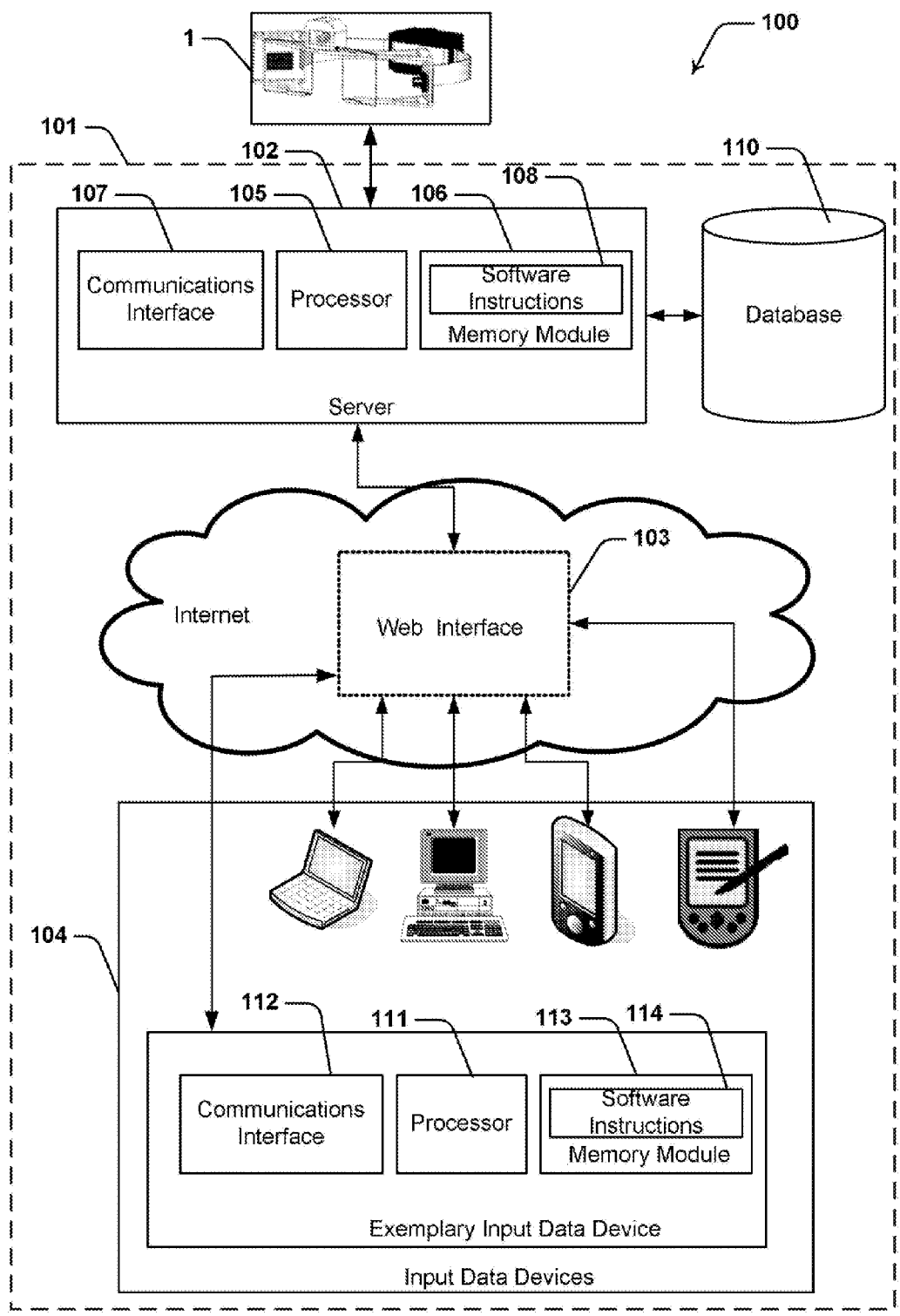
FIG. 6 illustrates a first exemplary implementation of the system of FIG. 5.
Figure 7:
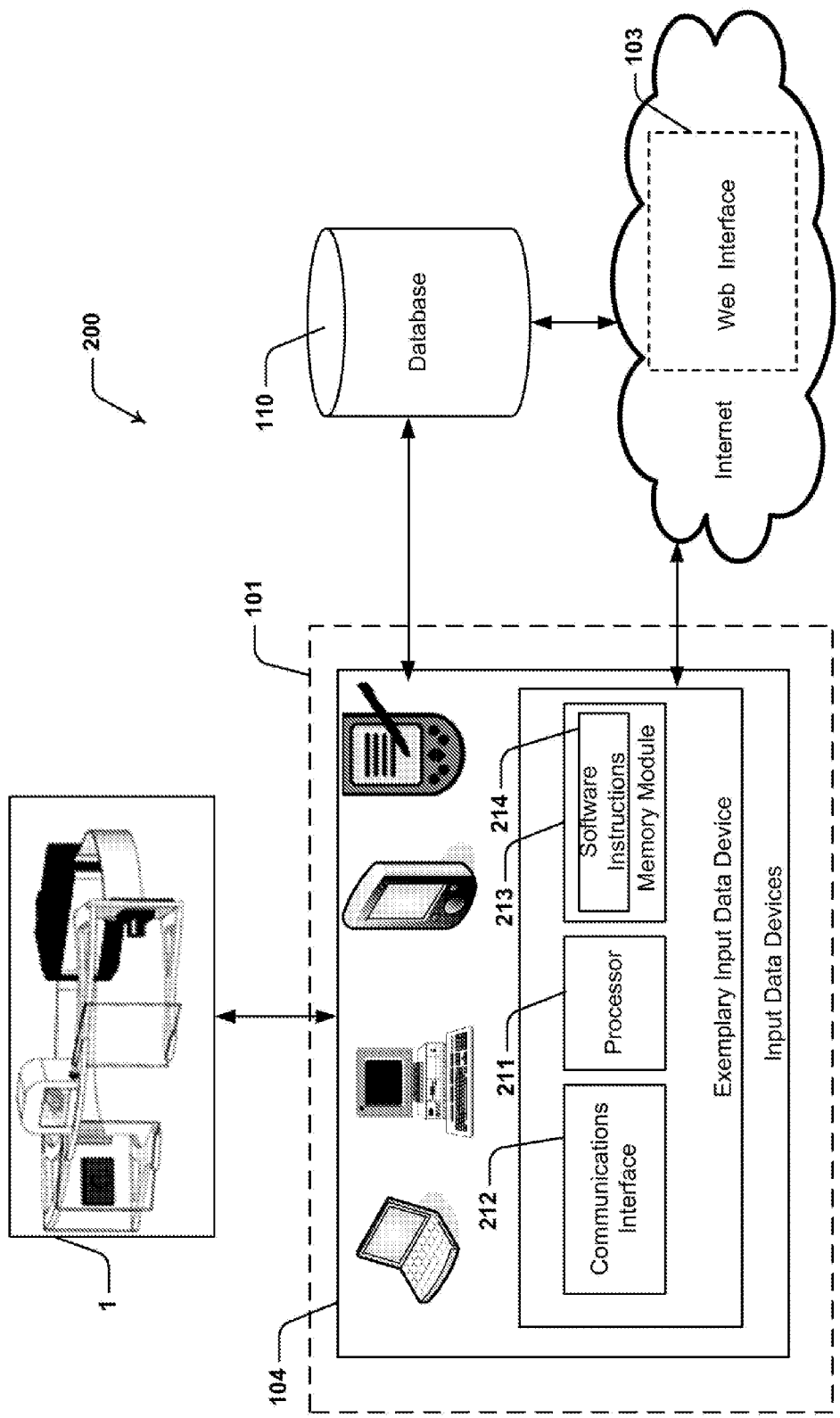
FIG. 7 illustrates a second exemplary implementation of the system of FIG. 5.

Referring now to FIGS. 6 and 7, there is illustrated schematically two systems for measuring a retinal image stability of a patient. FIG. 6 illustrates a first system 100 having a first configuration and FIG. 7 illustrates a second system 200 having a second system configuration. Systems 100 and 200 both include measurement device 1 that is adapted to be worn by the patient. As described above, device 1 includes sensors for obtaining eye motion and head motion data during a physical action by the patient in response to a visual and/or audio prompt as described below. Target module 8 includes a laser that selectively moves a laser beam across a screen in response to the sensed head motion. While systems 100 and 200 are described for use with device 1 of FIGS. 1 to 5, it will be appreciated that, in other embodiments, other devices are used in place of device 1. These other devices are capable of simultaneously obtaining eye motion and head motion data in response to a prompted motion.

Referring initially to FIG. 6, in system 100, a control module 101 is in communication with device 1 for processing the eye and head motion data during the physical action to provide an indication of the retinal image stability for the patient. The indication of retinal image stability includes one or more of the vestibulo-ocular reflex gain, latency, compensatory saccade amplitude and compensatory saccade latency of the patient. As mentioned above, device 1 is also capable of obtaining data indicative of other characteristics such as the patient's head translation and orientation during the motion. During the physical action, the position of laser spot 33 is controlled and the position data is stored in memory 27.

Control module 101 is adapted to communicate with an interface on a computer, for prompting the patient to perform a specific physical action from a number of predefined physical actions. In system 100, device 1 is communicable with control module 101 through an intermediate web server 102 providing the interface.

In overview, web server 102 provides a web interface 103. This web interface is accessed by users by way of client terminals 104. Here the term 'users' refers to the patient themself and/or clinicians, professionals and other persons assisting the patient. Users access interface 103 over the Internet by way of client terminals 104, which in various embodiments include the likes of personal computers, PDAs, cellular telephones, gaming consoles, and other Internet enabled devices. The client terminals 104 each include an input/output interface that is capable of providing visual and/or audio output to users. As illustrated, control module 101 includes client terminals 104, server 102 and interface 103.

Server 102 includes a processor 105 coupled to a memory module 106 and a communications interface 107, such as an Internet connection, modem, Ethernet port, wireless network card, serial port, or the like. In other embodiments distributed resources are used. For example, in one embodiment server 102 includes a plurality of distributed servers having respective storage, processing and communications resources. Memory module 106 includes software instructions 108, which are executable on processor 105.

Server 102 is coupled to a database 110. In further embodiments the database leverages memory module 106.

In some embodiments, web interface 103 includes a website. The term "website" should be read broadly to cover substantially any source of information accessible over the Internet or another communications network (such as WAN, LAN or WLAN) via a browser application running on a client terminal. In some embodiments, a website is a source of information made available by a server and accessible over the Internet by a web-browser application running on a client terminal. The web-browser application downloads code, such as HTML code, from the server. This code is executable through the web-browser on the client terminal for providing a graphical and often interactive representation of the website on the client terminal. By way of the web-browser application, a user of the client terminal is able to navigate between and throughout various web pages provided by the website, and access various functionalities that are provided.

In other embodiments, web interface 103 includes a proprietary software application such as an iPhone app that is downloadable onto one or more client terminals 104 for use by the users.

In general terms, each terminal 104 includes a processor 111 coupled to a memory module 113 and a communications interface 112, such as an Internet connection, modem, Ethernet port, serial port, or the like. Memory module 113 includes software instructions 114, which are executable on processor 111. These software instructions allow terminal 104 to execute a software application, such as a proprietary application or web browser application and thereby render on-screen a user interface and allow communication with server 102. This user interface allows for the creation, viewing and administration of profiles, access to the internal communications interface, and various other functionalities.

Referring now to FIG. 7, system 200 includes a second system configuration wherein device 1 is in direct communication with client terminals 104 and terminals 104 function, at least in part, as the control module 101. In this configuration, proprietary software methods are implemented on client terminals 104. For example, in such embodiments client terminals 104 maintain software instructions for a computer program product that performs the various functions including controlling mirror 11 on device 1 and processing data from device 1 to provide an indication of retinal image stability for the patient (for instance via an iPhone app or the like).

Client terminals 104 are in communication with an external database 110 and web interface 103. Database 110 allows for storage of data obtained by device 1 in conjunction with prompting and exercise information provided by client terminals 104. In one embodiment, database 110 is a local data storage system in direct communication with client terminals 104 and accessible by web interface 103. In another embodiment, database 110 is a remote data storage facility accessible by client terminals 104 and web interface 103 through servers, cloud servers and/or the Internet. In a further embodiment, database 110 includes a collection of spatially separate storage servers linked together so as to be accessible as a single data source. In this latter embodiment, the storage servers may be located in separate states, territories, countries or jurisdictions. In some embodiments, database 110 is maintained by either the clinician or a third party, e.g., the device manufacturer.

In system 200, web interface 103 is adapted to send instructions to control module 101 and/or retrieve patient assessment and rehabilitation information from control module 101 and database 110. Web interface 103 allows other users such as a clinician treating the patient to monitor the patient's progress and provide input to the patient's treatment plan.

Figure 8:
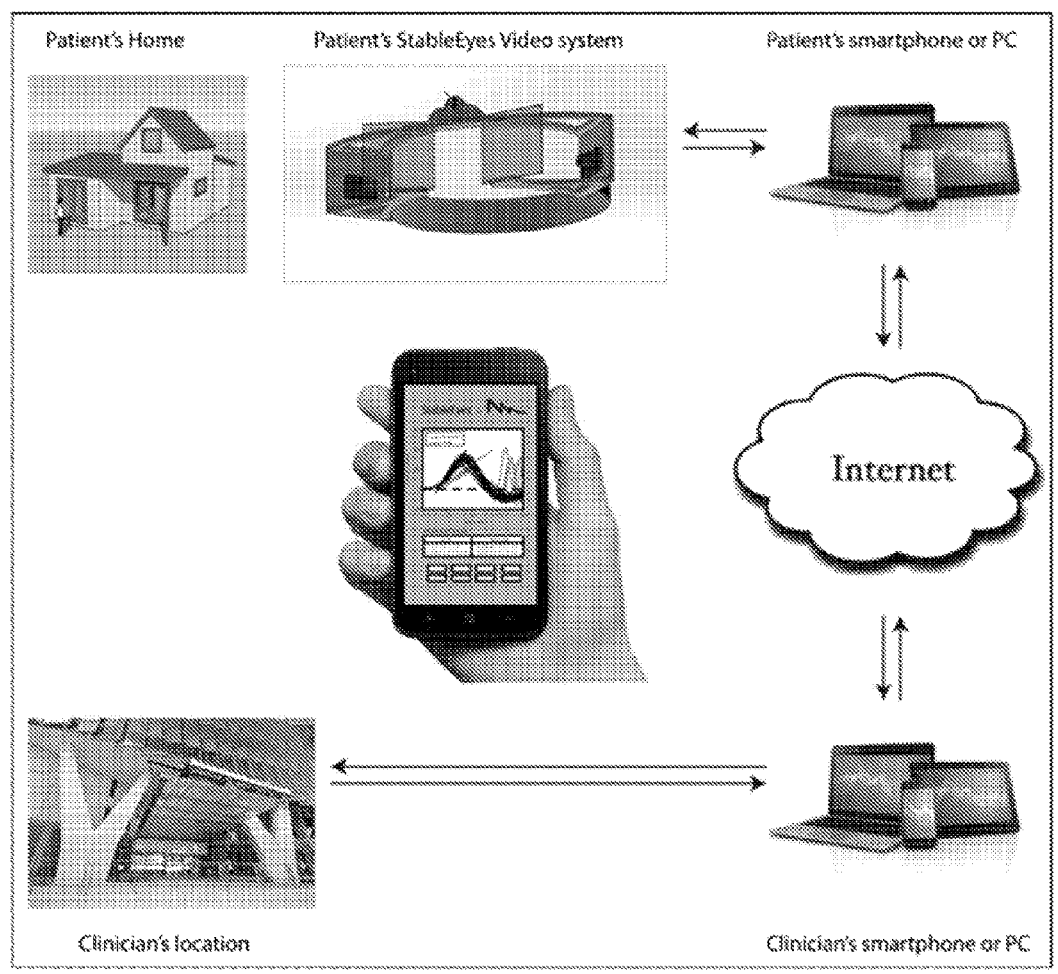
FIG. 8 illustrates a functional flow diagram of the system of FIG. 5.

This input and output functionality is shown schematically in the functional flow diagram of FIG. 8. Here, the patient uses device 1 in their home to conduct the assessment and/or rehabilitation exercises. Device 1 communicates the obtained head and eye motion data and laser spot position data to a nearby Smartphone or PC, which operate as the control module 101. The Smartphone or PC also provides instructions to the patient for performing the required exercises (audibly and/or visually). A clinician is able to access and/or communicate with the patient's Smartphone or PC from their computer device at a remote location through the web interface to monitor and control the patient's treatment.

Exemplary use of device 1 and system 200 will now be described. It will be appreciated that a corresponding equivalent implementation is possible using system 100 of FIG. 6 wherein patients and other users (clinicians and the like) all access device 1 through web interface 103 and server 102.

In use, device 1 is placed on the patient's head and 7 secured in place with strap 45 such that cameras 13 and 15 are positioned as shown in the plan view of FIG. 4. The patient situates themselves at a distance of about 1 meter from substantially flat wall 31 and is preferably seated. Once device 1 is activated, laser spot 33 is projected onto the wall in front of patient 3. The surrounding lighting is preferably dimmed or switched off to enhance the patient's concentration on laser spot 33. Patient 3 has access to a client terminal 104 in the form of a Smartphone, tablet or personal computer located nearby. The client terminal 104 is configured with software that provides visual and/or audio instructions through a screen and/or speaker to prompt the patient to perform predefined actions or exercises. Alternatively, audio instructions are provided to patient 3 through speaker 51 on device 1. Client terminal 104 also links wirelessly with device 1 to control the position of laser spot 33 on wall 31 during an exercise.

Figure 9:
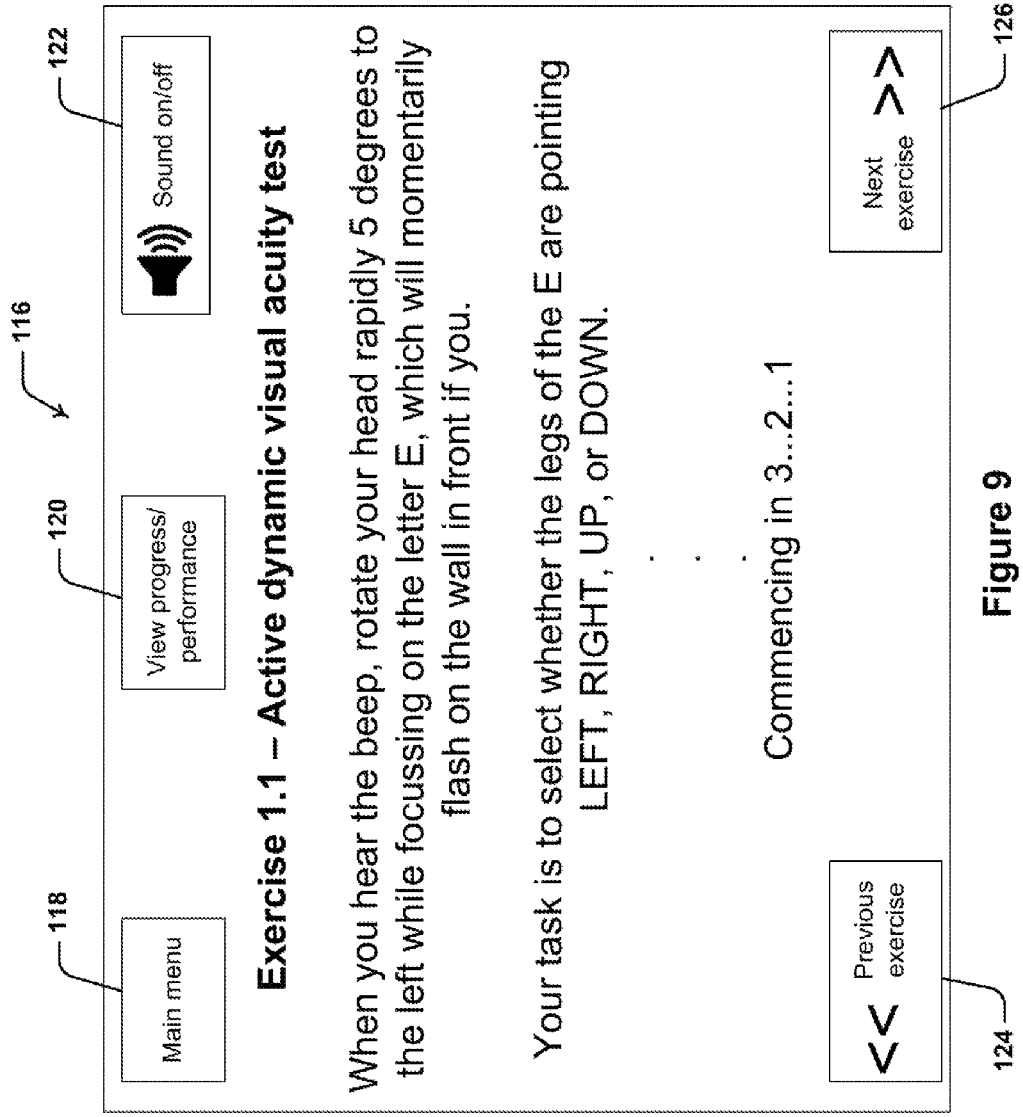
FIG. 9 illustrates an exemplary screen displayed on a client terminal in the system of FIG. 7.

An exemplary screen 116 displayed on a client terminal is illustrated in FIG. 9. Screen 116 illustrates the current exercise number and name, as well as visual instructions for performing the current exercise. Screen 116 provides a number of buttons selectable by the patient or other user to perform various functions. A 'main menu' button 118 navigates the user to a main menu providing options to further navigate the user to various screens or pages. A 'view progress/performance' button 120 navigates the user to a screen or series of screens displaying the patient's progress through the exercises and performance of the completed exercises. A 'sound on/off' button 122 allows the audio instructions to be switched on or off. A 'previous exercise' button 124 navigates the user to the previous exercise, allowing the user to perform the exercise again. A 'next exercise' button 126 navigates the user to the next available exercise. Control of these various functions is set by an administrator such as a clinician.

During an initial use, or after a predetermined amount of time, patient 3 may be prompted to perform a calibration procedure by undertaking predetermined head and/or eye movements in response to the prompts. The calibration procedure calibrates the system so that the relative positions of the laser spot, patient's eye and head motion are precisely measured.

At the commencement of each exercise, control module 101 prompts the patient 3 to perform a physical head motion action while focussing on laser spot 33. In response to the head motion sensed by head tracking module 16, mirror 11 is selectively tilted to move laser spot 33 with respect to the head motion. Depending on the particular exercise, the laser spot may move (synchronously or asynchronously) or remain stationary during the patient's head motion. In other exercises, the patient may be instructed to keep their head stationary while tracking movement of the laser spot 33 with their eyes. In exercises where the head is to remain stationary, the position of laser spot 33 is controlled by control module 101 and is configured to trace predetermined paths across wall 31.

During each exercise, signals indicative of head motion are generated by the gyroscope, magnetometer and accelerometer, and are passed to IC 17. The received signals are adapted to have a voltage with a polarity that is dependent on the direction of head rotation. The received signals are transmitted to control module 101 through communications interface 21. In some embodiments, the signals obtained are sampled at predetermined intervals for aiding in the comparison of datasets. The signals may undergo other processing such as filtering and rectification. In other embodiments, including digitally controlled designs, the voltage of the received signals does not change polarity based on the direction of head rotation.

Concurrently, during each exercise, the patient's eye gaze is tracked by detecting infra-red radiation that is transmitted from LEDs 59 and 61, reflected off the patient's eyes, and captured as infra-red images of the eyes using cameras 13 and 15. Images gathered by cameras 13 and 15 and their sample time transmitted to the control module 101 where a pupil tracking algorithm is performed on the images in near real-time to ascertain the direction of the patient's eye gaze. In most cases, this is performed by the patient's PC, Smartphone or other computer device utilising the relevant software. However, in some cases the data may be transferred to an external server where the processing is performed.

Provided device 1 is calibrated correctly, because of the fixed relative spatial-geometry between the head tracking, eye tracking and target modules, a comparison of the patient's eye gaze direction with the known position of laser spot 33 allows an assessment of the patient's accuracy in tracking the laser spot. This is a point of difference over other known measurement devices, which cannot accurately determine whether the patient's actual eye movement is fixating/tracking the visual target during assessment and rehabilitation.

Following each exercise, control module 101 compares the laser spot position (or signal driving the target module 11) with the head motion data obtained from head tracking module 16 and the eye motion data from eye tracking module 12 to produce an indication of retinal image stability for the patient. This indication includes estimations of the VOR gain, latency, compensatory saccade amplitude and compensatory saccade latency of the patient.

Figure 10:
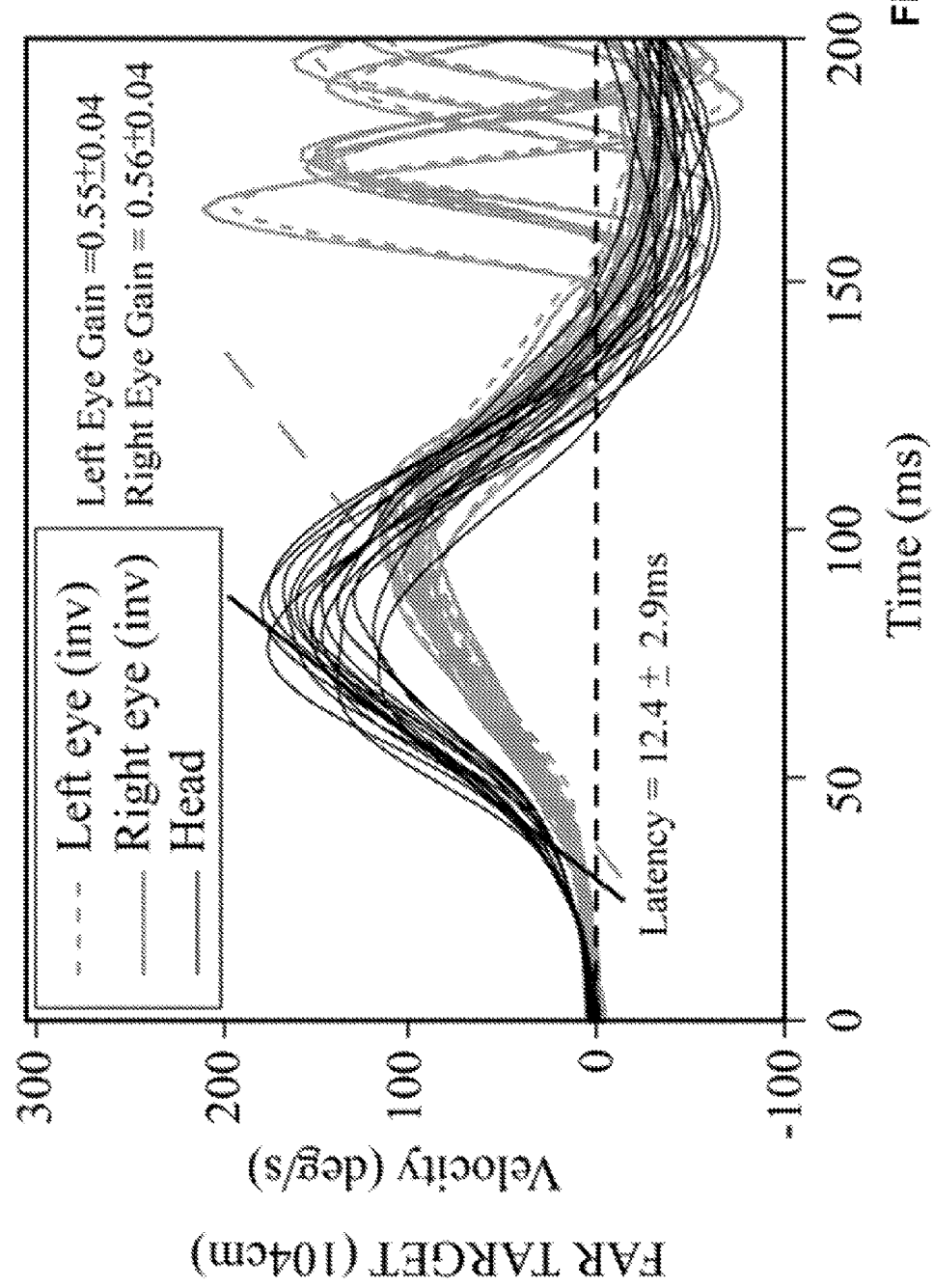
FIG. 10 illustrates a graph of head impulse data from a patient with left horizontal VOR hypofunction.

As an example measurement, FIG. 10 illustrates a graph of head impulse data from a patient with left horizontal VOR hypofunction. The head impulse consists of either an active (self-generated) or passive (manually delivered by an assistant) transient head rotation with peak-amplitude of about 5 degrees, peak-velocity of about 150 degrees/second and peak-acceleration of about 3000 degrees/second$^2$, while looking at the target object. Each semicircular canal of the patient's vestibular system is tested by delivering the head impulse in the plane of one of the canal pairs: yaw (horizontal rotations maximally stimulating the left or right horizontal canals), LARP (left anterior and right posterior canals) and RALP (right anterior and left posterior canals) planes.

In FIG. 10, the black trace denotes head velocity and the grey traces denote left (dashed) and right (solid) eye velocities, which have been inverted in sign to facilitate comparison between head and eye data. The VOR gain is calculated by dividing the relevant component of inverted eye velocity by head velocity during a 30 ms period prior to peak head velocity. That is, about 50 to 80 ms after the head impulse onset. For example, to calculate the leftward horizontal VOR gain, eye and head angular velocity is calculated during a leftward head impulse and the inverted horizontal component of eye velocity is divided by the horizontal component of head velocity. The VOR latency is calculated by fitting (with a least squares algorithm) a line to the positive acceleration part of the eye velocity traces and the head velocity traces. In the illustrated example, the positive acceleration part of the head velocity trace occurs at around 40 to 70 ms after head impulse onset. However, the positive acceleration part of the eye velocity trace occurs at about 50 to 100 ms after the stimulus onset. The latency is defined as the difference in time where these lines intersected with the zero velocity baseline. Approximately 15 head impulses towards each direction (e.g., 15 leftwards and 15 rightwards when testing the horizontal VOR) are required to reliably determine the mean gain and latency values (i.e., standard deviation <10% of mean). Compensatory saccades happen in this patient approximately 150 ms after head impulse onset.

As described below, a number of different types of prompted physical actions are able to be provided to the patient and the choice depends on the purpose of the exercise. An assessment or diagnosis exercise may prompt the patient to perform a simple horizontal or vertical rotation of the head in a predefined direction, say to the left or downward, while watching a stationary laser spot. A more advanced rehabilitation exercise may prompt the patient to perform more complex head movements while tracking a moving laser spot with the eyes. Another example of the prompted physical action is a substantially horizontal or vertical rotation of the eyes in a predefined direction while keeping the head stationary.

In some exercises, the patient's head velocity is fed back to device 1 for determining a direction and speed of laser spot 33. That is, device 1 senses angular head velocity and, in response, projects laser spot 33 along a predetermined trajectory that requires a predetermined VOR gain for optimal image stabilisation.

Through the application software, control module 101 is able to retrieve and store data on device 1, analyse data, provide summary information and data trends to the patient, clinicians and other parties over the Internet. System 200 also provides for making the patient data (including raw data obtained from device 1 and the retinal image stability indications derived from this data) available to other parties through access by database 110 and web interface 103. The data stored and shared is subject to certain degrees of confidentiality as applicable in the relevant situation and/or jurisdiction.

The level of patient control is able to be set, through the software, by the clinician or another user and can range from none to complete control. Complete control would allow the patient to set the device mode (testing or training), mode setting (e.g., in 'training mode' exemplary exercises include: Smooth pursuit, saccades, active VOR, passive VOR, combined Smooth Pursuit and VOR) and exercise parameters (e.g., in 'training mode' and 'VOR setting' parameters include: head rotation type (active or passive), initial VOR gain, training epoch duration, increase in VOR gain between subsequent epochs, total number of training epochs).

The clinician or another authorised party is able to, through respective software installed on a respective PC, Smartphone or other computer device, remotely access data from each device 1 via database 110. The data accessible to the clinician or other authorised party includes device settings, exercises to be performed, exercise parameters and logged data (e.g., date, testing/training start and end times, mode, settings, parameters, target, eye and head motion data). The clinician software, installed on an internet connected Smartphone, PC or other computer device, provides summary data to help monitor patient progress and allow the clinician to change device settings and exercises remotely, especially for patients that are not technically inclined.

Exemplary VOR Assessment, Adaptation and Training Exercises

Figure 11:
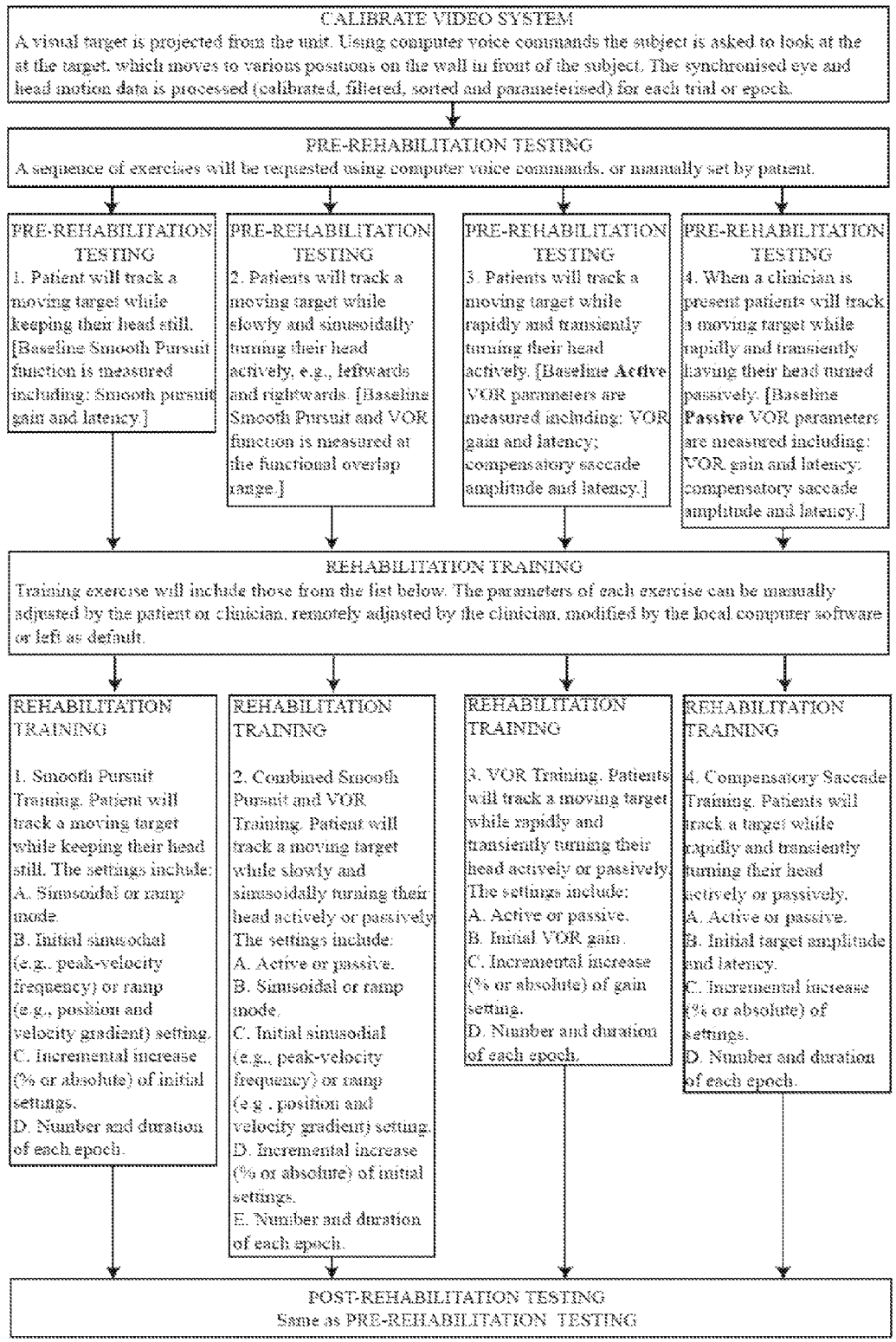
FIG. 11 illustrates an exemplary flow chart of the processes involved in patient testing using the device of FIGS. 1 to 4 and the system of FIG. 7.

Using the device and systems described above, a number of assessment and training exercises are able to be performed on patients to assess their retinal image stability and VOR, and to rehabilitate and train the patient to improve those characteristics. FIG. 11 illustrates an exemplary flow chart of the processes involved in patient testing using device 1 and system 200. After calibration is performed, the testing procedure is broken down into two main steps: a pre-rehabilitation testing process (assessment or diagnosis); and a rehabilitation training process. Each of these steps includes a number of different programs or exercises. Some exemplary exercises for each of the two steps will now be described. In some exercises, additional target objects are used either together with the laser spot or instead of the laser spot.

Pre-Rehabilitation Testing (Assessment and Diagnosis)

Dynamic Visual Acuity Test

Dynamic visual acuity is measured using optotype characters presented only when the head is moving within a certain range of rotational velocities. Passive dynamic visual acuity is tested when the operator moves the head, whereas active dynamic visual acuity is tested with self-generated head movement.

Head Impulse Test

The Head Impulse Test is able to test a patient's passive and active VOR. The Head Impulse Test has two main advantages over other vestibular tests: 1) the stimulus frequency includes the physiologically relevant spectral range of 1 to 15 Hz, and 2) the test allows measurement of individual semicircular canal function. The passive head impulse test/exercise consists of a manual, passive, unpredictable, uni-directional 5 degree head rotation with peak-acceleration in the order of 3000 degrees/s$^2$. The active head impulse test/exercise consists of the same head rotation except that it is a self-generated, active and predictable. Each semicircular canal can be tested in isolation by rotating the head in the plane of that canal, and towards that canal. For example, the right horizontal canal can be tested by rotating the head to the right and measuring the magnitude of the leftward eye movement generated by the VOR.

Rehabilitation Training

Smooth Pursuit Measurements

While keeping their head still, the patient tracks a laser spot moving sinusoidally (i.e., moves repeatedly in two directions, e.g., leftwards then rightwards) or ramp (i.e., moves once in one direction, e.g., leftwards only). The target velocity gradually increases from 20 degrees/second up to 200 degrees/second and for sinusoids the target frequency increases from 0.2 Hz to 2.0 Hz. After removing saccades or quick-phases from the data (quick-phases have similar characteristics to saccades and can be removed using the same technique) the smooth pursuit gain is calculated by dividing the average (line-fitted or sinusoid fitted) eye velocity by the laser target velocity.

Saccade Measurements

While keeping their head still, the patient tracks a laser spot that is presented onto the wall. The spot extinguishes and then changes position with variable amplitude before being re-illuminated onto the wall (i.e. the target appears to 'jump' in two directions, e.g. left then right or up then down). Knowing the position of the laser target and the head, saccade accuracy, velocity, and amplitude can be determined.

Incremental Adaptation

Incremental adaptation training consists of a number of epochs (e.g. 10 epochs). Each epoch transpires for a predetermined time period (e.g. 90 seconds) and successive epochs are incrementally more challenging than the previous epoch.

Unilateral Adaptation

It has been identified that, in patients with unilateral hypofunction (having one side of their vestibular system impaired relative to the other side), the VOR should be increased for rotations to the impaired side only, as increasing the VOR gain for rotations towards the normal side results in inappropriately larger eye movements. The present inventors have proposed a rehabilitation exercise involving a unilateral (asymmetric) retinal slip stimulus that incrementally increases the VOR only for rotations towards the impaired ear. In these exercises, movements involving head rotations to one side (adapting side) are performed, but for rotations towards the other (non-adapting) side, the VOR stimulus was removed or kept at a fixed level of difficulty (VOR gain for optimal visual stabilisation kept at unity).

Using device 1, laser spot 33 is moved at a speed that required a predetermined VOR gain for optimal image stabilisation that could be set differently for leftward and rightward head rotations. For head rotations in the adaptive side (the impaired side that is to be rehabilitated), the speed of laser spot 33 is incrementally varied and the VOR gain is measured. For head rotations in the non-adaptive side (the non-impaired side), the speed of laser spot 33 is maintained constant so that little or no changes in the patient's VOR gain is experienced. For example, the target gain is adjusted asymmetrically with a VOR gain of 1.5 for image stabilisation during rightward head rotations, and a VOR gain of 1.0 during leftward head rotations.

In one exemplary unilateral adaptation exercise, patients are prompted to make active (self-generated) head impulses from a neutral, neck-centred starting position alternating to the left and right. The patient commences each head impulse when the head is in the neutral position and a flashing laser target appears. When head velocity exceeds a preset threshold, e.g., 120 degrees/s, the laser turns off for about 2 seconds. The velocity threshold is chosen so that the effects of non-vestibular systems such as smooth pursuit, optokinetic and predictive oculomotor systems are minimal because these generally operate at lower velocities than the VOR. During these 2 seconds the patient completes the rest of the impulse (the entire impulse duration is about 150 ms), pauses and slowly returns their head back to the neutral position.

In an alternate method, the patient commences each head impulse when the head is in the neutral position and a flashing laser target appears. When head position exceeds a preset threshold, e.g., 5 degrees, the laser turns off until the head is rotated back to the neutral position.

Reappearance of the laser target is the cue to perform an impulse head motion to the opposite side. During the head impulse, the patient's task is to either fixate on the visible laser target or fixate on the last remembered location of the laser target before it turned off. During horizontal VOR training the vertical laser position moves in the same direction and magnitude as the (undesired) head pitch movement. During horizontal VOR training the horizontal laser position is controlled by horizontal head velocity and the preset head direction adaptation gain. Patients are preferably prompted to perform a large number, e.g. 300, active head impulses. i.e., 150 impulses to each side, over the entire training session. The non-adapting side gain is set so that the VOR gain required for target image stabilisation is about 1.0.

Alternatively, for rotations towards the non-adapting side the laser can be turned off so that there is no target. The adapting side gain is initially set at the VOR gain level of the patient, which will be <1 because their VOR is not functioning normally, and then increased for each subsequent training epoch by a fixed value or a preset percentage of the previous training epoch, e.g., a 10% increase between epochs. For example, if the patient's VOR gain before training was 0.5, and there were 10 training epochs lasting 90 seconds each, and there was a 20% increase in the difficulty of the vision stabilisation task during head impulses between epochs, then the vision stabilisation task would require a VOR gain of 0.60 during epoch 1, 0.70 during epoch 2, and so on until epoch 10, which would require a gain of 1.5. The adaptation training typically takes about 15 minutes.

Conclusions

It will be appreciated that the disclosure above provides various significant improved systems and methods for diagnosis and therapy of vision stability dysfunction.

The device and system described above allows for accurate monitoring of the patient's actual eye movement during assessment and rehabilitation. This new feature in monitoring the patient's eye motion leads to more accurate VOR and retinal image stability assessments. It also provides for measuring and monitoring responses during head movement in planes other than a horizontal plane, and also facilitating remote intervention, assessment and program planning by a clinician situated at a location geographically removed from that of the patient.

Device 1 is controlled wirelessly by a corresponding software application installed on a client terminal (Smartphone, PC, or other computer device). The client terminal is in turn linked to a database X over the Internet. A clinician assessing the patient can remotely monitor patient progress and alter the device settings and/or exercises to be performed to improve customised patient rehabilitation.

Unlike other designs, in device 1 the target module 8, including laser 9, is integral with the device and controlled through IC 17 and external processor 23. This allows for better tracking of the patient's actual response (head and eye motion) to the prompted motion. That is, with device 1, it is easier to determine how accurately the patient is performing the prompted motion. By separating out this factor from the obtained data, the patient's response performance can be more accurately determined.

The integral nature of target module 8 also allows for the accurate implementation of unilateral adaptation rehabilitation techniques.

Interpretation

Unless otherwise defined all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein. For the purposes of the present invention, additional terms are defined below. These definitions are provided as general definitions and should in no way limit the scope of the present invention to those terms alone, but are put forth to facilitate a better understanding of the following description.

The use of the word 'about' to qualify a number is merely an express indication that the number is not to be construed as a precise value and should be read in the context of the accuracy with which a skilled addressee would assess such a term.

Unless the context provides otherwise, use of the terms "induce", "induced", "inducing" and the like, and "prompt", "prompted", "prompting" and the like are intended to be used in the sense of encouraging an act rather than physically bringing about an act. For example, if a user is prompted or induced to perform a head motion, that user is given instructions and the user may choose to respond to those instructions.

Unless specifically stated otherwise, as apparent from the following discussions, it is appreciated that throughout the specification discussions utilizing terms such as "processing," "computing," "calculating," "determining", analysing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one or more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fibre optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A device for obtaining vestibulo-ocular reflex data from a patient having a head and at least one eye, the device including:
    a frame configured for mounting to the patient;
    a target module mounted to the frame and being responsive to a drive signal to project a selectively movable target object onto a surface in front of the patient;
    an eye tracking module mounted to the frame, the module being adapted for obtaining first data indicative of one or more characteristics of the at least one eye; and
    a head tracking module mounted to the frame, the head tracking module being adapted for obtaining second data indicative of one or more characteristics of the motion of the head.

2. A device according to claim 1 including an analysis module that is responsive to the drive signal and at least a subset of both the first data and the second data for providing an indication of retinal image stability for the patient.

3. A device according to claim 2 wherein the indication of retinal image stability includes one or more of the visual, non-visual, sinusoidal or impulse vestibulo-ocular reflex gain, nystagmus, phase and nystagmus latency, compensatory saccade amplitude, compensatory saccade latency, smooth pursuit gain, smooth pursuit latency, smooth pursuit phase, saccade accuracy, saccade latency, or saccade velocity.

4. A device according to claim 1 wherein the target module includes a laser configured to project at least one laser beam onto the surface to define the target object.

5. A device according to claim 4 wherein the direction of the at least one laser beam is electrically controllable by the drive signal.

6. A device according to claim 4 wherein the drive signal is generated in response to the motion of the head detected by the head tracking module.

7. A device according to claim 1 wherein the eye tracking module includes one or more cameras positioned to capture video images of the at least one eye.

8. A device according to claim 7 wherein the one or more characteristics of the at least one eye include the eye gaze direction.

9. A device according to claim 7 wherein the eye tracking module includes one or more hot mirrors that transmit visible radiation and reflect infra-red radiation and wherein the one or more cameras are configured to detect infra-red images of the at least one eye reflected off the one or more hot mirrors.

10. A device according to claim 9 wherein the one or more hot mirrors are positioned in the line of sight between the at least one eye and the target object, and the one or more cameras are positioned out of the line of sight between the at least one eye and the target object.

11. A device according to claim 10 including a pair of hot mirrors and a pair of cameras oppositely disposed on the frame for simultaneously measuring first data for both a left and right eye of the patient.

12. A device according to claim 11 wherein the frame includes a mount for maintaining a corresponding one of the hot mirrors in the line of sight of a respective one of the left and right eyes, the mount further maintaining the cameras at peripheral positions outside the lines of sight of the left and right eyes.

13. A device according to claim 1 wherein the one or more characteristics of the motion of the head include a translational position, translational velocity and translational acceleration of the head in three dimensions and an angular position, angular velocity and angular acceleration of the head in three dimensions.

14. A device according to claim 1 wherein the drive signal is derived from motion of the head detected by the head tracking module.

15. A device according to claim 1 wherein the target module includes a display for displaying a virtual reality scene about the user and the target object is a virtual target within that scene.

16. A system for measuring a retinal image stability of a patient, the system including:
  a measurement device adapted to be worn by the patient, the measurement device including a sensor module for obtaining data indicative of one or more characteristics of at least one eye of the patient and the head of the patient during a physical action by the patient in response to a stimulus from a visual target object the measurement device further including a target module mounted thereon, the target module being responsive to a drive signal to project the target object onto a surface in front of the patient, the target being selectively movable by the target module to be tracked by the patient's eyes; and
  a control module in communication with the measurement device for processing data indicative of the one or more characteristics during the physical action to provide an indication of the retinal image stability for the patient.

17. A system according to claim 16 wherein the one or more characteristics includes the gaze direction of the at least one eye during the physical action and the position of the head during the physical action.

18. A system according to claim 16 wherein the control module is adapted to communicate with an interface for visually or audibly prompting the patient to perform a specific physical action from a number of predefined physical actions.

19. A system according to claim 16 wherein the control module includes software configured to remotely control the target module.

20. A system according to claim 19 wherein the target module includes a laser configured to project at least one laser beam onto a surface in front of the patient to define the target object.

21. A system according to claim 16 wherein the drive signal is derived from motion of the head detected by a head tracking module or motion of the eye detected by an eye tracking module, or both.

22. A system according to claim 21 wherein the target module is configured to deactivate the target object or move the target object, with respect to a patient's head, at a velocity that is a function of the patient's head motion velocity or patient's eye motion, or both.

23. A system according to claim 22 wherein the velocity of the motion of the target object is incrementally increased or decreased in response to the detected motion of the head or the detected motion of the eye, or both.

24. A method of rehabilitating a patient using a system for measuring a retinal image stability of a patient, the system including: a measurement device adapted to be worn by the patient, the measurement device including a sensor module for obtaining data indicative of one or more characteristics of at least one eye of the patient and the head of the patient during a physical action by the patient in response to a stimulus from a visual target object the measurement device further including a target module mounted thereon, the target module being responsive to a drive signal to project the target object onto a surface in front of the patient, the target being selectively movable by the target module to be tracked by the patient's eyes; and a control module in communication with the measurement device for processing data indicative of the one or more characteristics during the physical action to provide an indication of the retinal image stability for the patient, the method comprising:
  configuring the target module to electronically move the target object at a first velocity;
  configuring the sensor module to measure the patient's head motion velocity or eye motion, or both, while the patient tracks the target object; and
  in response to the measured head or eye motion, or both, incrementally increasing or decreasing the first velocity.

* * * * *